United States Patent [19]

Flossdorf et al.

[11] Patent Number: 5,087,425
[45] Date of Patent: Feb. 11, 1992

[54] DEVICE FOR FLOW-INJECTION ANALYSIS

[75] Inventors: Josef Flossdorf; Neophytos Papamichael; Detlef Hanisch; Henning Schillig, all of Brunswick, Fed. Rep. of Germany

[73] Assignee: Gesellschaft fur Biotechnologische Forschung mbH (GBF), Brunswick, Fed. Rep. of Germany

[21] Appl. No.: 391,585

[22] PCT Filed: Oct. 28, 1988

[86] PCT No.: PCT/EP88/00979
§ 371 Date: Aug. 28, 1989
§ 102(e) Date: Aug. 28, 1989

[87] PCT Pub. No.: WO89/04492
PCT Pub. Date: May 18, 1989

[30] Foreign Application Priority Data

Nov. 5, 1987 [DE] Fed. Rep. of Germany ....... 3737604

[51] Int. Cl.$^5$ .................. G01N 21/24; G01N 21/26; G01N 35/08
[52] U.S. Cl. .................. 422/81; 422/82.01; 422/82.03; 422/82.05; 422/82.06; 436/52

[58] Field of Search ............ 422/81, 82, 82.01, 82.03, 422/82.05, 82.06; 436/52, 53; 204/67, 403, 409, 410

[56] References Cited

U.S. PATENT DOCUMENTS

| 4,229,179 | 10/1980 | Lee | 422/82 |
| 4,233,001 | 11/1980 | Schmid | 422/82 |
| 4,314,824 | 2/1982 | Hansen et al. | 422/81 |
| 4,865,811 | 9/1989 | Newton et al. | 422/82 |

FOREIGN PATENT DOCUMENTS

| 1498603 | 11/1970 | Fed. Rep. of Germany . | |
| 0132210 | 9/1978 | Fed. Rep. of Germany | 422/81 |
| 0135858 | 6/1988 | Japan | 422/81 |
| 0173852 | 7/1989 | Japan | 422/81 |
| 2189597 | 10/1987 | United Kingdom . | |

Primary Examiner—David L. Lacey
Assistant Examiner—Kimberly A. Trautman
Attorney, Agent, or Firm—Kane, Dalsimer, Sullivan, Kurucz, Levy, Eisele and Richard

[57] ABSTRACT

The invention relates to a device for flow-injection analysis having a reaction loop, one or more pumps, an injection valve, one or more detectors and an evaluating device.

16 Claims, 3 Drawing Sheets

DEVICE FOR FLOW-INJECTION ANALYSIS

BACKGROUND OF THE INVENTION

1. Field of the Invention

The invention relates to a device for flow-injection analysis, comprising a reaction loop, one or more pumps, an injection valve, one or more detectors and an evaluating device.

2. Brief Description of the Prior Art

Flow-injection analysis (FIA) is a wet-chemical analysis method which in recent years has developed into a valuable and frequently used method. In flow-injection analysis, the sample to be analysed is injected into a stream of a suitable liquid (carrier liquid) and is introduced, together with the latter, into a detection system. The structure of a device for flow-injection analysis is therefore similar to that of a liquid chromatography arrangement, the separating columns being replaced, however, by a reaction loop. The (generally peristaltic) pump serves to drive the carrier liquid. The sample to be analysed is injected through the injection valve (generally a rotary 2- or 3-way valve) into the carrier liquid. The detector indicates the passage of the sample, and in the evaluating device the analytical content of the sample is detected quantitatively. This functional principle is illustrated diagrammatically in FIG. 1 (from J. Ruzicka and E. H. Hansen 'Flow Injection Analysis' in 'Chemical Analysis', Volume 62, John Wiley and Sons, New York, 1981), R being the carrier or reagent stream, S the site for injection of the sample, FC a through-flow cell and W the liquid waste. In the simplest method of flow-injection analysis the carrier stream might contain a reagent that reacts with the substance to be analysed to form dyestuff. An analysis reaction could be, for example, the expulsion of thiocyanate from $Hg_2(^I)(SCN)_2$ by $Cl^-$ ions. After the addition of $Fe^{3+}$ ions a blood-red coloring is produced and the photometer measures a wave-length of 480 nm. Although flow-injection analysis is not a continuous method of analysis, the repetition rate of the individual measurements is generally so high that for many purposes the method can be regarded as a quasi-continuous method.

Flow-injection analysis is not limited to applications in which a sample to be analysed is injected into a stream of liquid containing a reagent. With expensive reagents, it may be more advantageous to inject the reagent into the sample. If the reagent and the sample are expensive, the sample and the reagent can be injected simultaneously into a stream of carrier liquid by way of a dual-input valve. This is known as the 'Merging Zone' method.

It is not only photometers, as mentioned above, that are suitable as detectors but in fact any device that converts the chemical detection reaction quantitatively into an electrical signal. Detectors may be, for example, fluorimeters, refractometers, luminescence detectors, turbidity meters, pH and ion-sensitive electrodes, voltage-measuring and amperometric detectors, conductivity meters, thermistors, semi-conductor structures (FETs), etc.. Flow-injection analysis is not limited to wet-chemical detection means. The use of enzymes in dissolved or immobilized form, of immobilized antigens/antibodies, of organelles and of microorganisms means that the range of application of flow-injection analysis can be considerably extended.

Some known devices for flow-injection analysis are described in more detail below.

A basic device (type 5020) available from Tecator GmbH, 6054 Rodgau, comprises two multi-channel peristaltic pumps, an injection valve, a module for mixing the sample and reagent streams and a microprocessor control means, with the aid of which the analysis procedures can be preprogrammed. A diffusion stage, an extraction stage and a thermostat for heating the reaction loops can be added subsequently. A sample-input machine as well as a recorder and a printer can be connected externally. Depending on the mode of operation, the detector signal is evaluated in particular ways, for example the signal height, area, width and building-up time can be evaluated. The pumps, the injection valve and the control electronics are mounted in the device in a fixed manner. The housing dimensions are approximately 45 cm×45 cm×20 cm. If a multi-channel arrangement is used, a corresponding number of individual devices have to be arranged adjacent to one another.

A further known device for flow-injection analysis, from Chem Lab, has a 5-channel pump, an injection valve, heating devices for the reaction loops and a filter photometer with glass fiber optics and a through-flow cell, which are mounted in a fixed manner in a housing having the dimensions 30 cm×38 cm×18 cm. A recorder and a microprocessor can be connected to the photometer. An extension in the form of an autosampler and an optional coupling to a recorder and/or a data-detection and evaluation system are possible. If a multi-channel arrangement is to be used a plurality of complete devices have to be set up next to one another.

Hitachi also offers a basic device (dimensions 30 cm×40 cm×55 cm, Type K-1000) that contains, mounted in a fixed manner, a two-channel piston pump, a four-channel peristaltic pump, an injection valve and temperature-controlled reaction loops. An automatic sample indicator, a solvent-extraction unit and optical detectors (photometers, fluorescence spectrometers) can be connected externally. After-fitting with printers, plotters and data stations is possible. Multi-channel operation with the basic device alone, on the other hand, is not possible.

Flow-injection analysis can, as already mentioned, be used for a wide range of applications. The flexibility of the devices currently on the market is, however, unsatisfactory and not all the devices needed for analyses are available, for example enzyme reactors and detectors other than photometers. In addition, the desire for a multi-channel structure is on the increase and cannot be very adequately catered for with the known devices.

The problem on which the invention is based, therefore, is to provide a versatile device for flow-injection analysis which can be used for a variety of applications and which is economical to produce.

SUMMARY OF THE INVENTION

The problem is solved according to the invention in a device for flow-injection analysis of the type mentioned at the beginning, as follows:

the pump, the injection valve and the detector are each attached to a base plate provided with a guide means, the pump, the injection valve and the detector, each with its base plate, are of uniform width and height, the base plates with the pump, the injection valve and the detector are joined together on the support mounting to form the analysis arrangement, and the base plates are held on the support mounting by a releasable securing means.

The dependent claims relate to advantageous developments of the analysis device according to the invention.

DETAILED DESCRIPTION OF THE PREFERRED EMBODIMENTS OF THE INVENTION

The device according to the invention for flow-injection analysis is distinguished by a high degree of flexibility. The basic units, such as the pump, the injection valve, the detector, etc., are not mounted in a fixed manner but are merely put together in a row and assembled to form a device for a particular analysis and for the operation thereof. If the device is to be modified or if a different version of the device is to be made from the basic units, these basic units can be removed and put back again individually. This allows any desired version of a device for flow-injection analysis to be put together in simple manner and, furthermore, allows the individual basic units to be arranged logically, that is to say in the flow direction of the reagent stream (from the pump towards the detection system).

The flexibility of the device of the invention is also made possible especially by the fact that the shape and the external dimensions of the basic units match one another. They all have uniform dimensions as regards width and height, with the result that an analysis device according to the invention fits into standard plug-in units or takes up only part of such a plug-in unit, for example three units of height (approx. 132 mm) and ¼ of a 19-inch plug-in unit. With suitable dimensions it is therefore possible to accommodate several devices in one plug-in unit. All that is necessary then in the observance of the side constraint that the pumps and valves, thermostat, photometers, etc. that are purchased as additions should have internal dimensions that do not exceed 10 cm × 10 cm. The depth of the device is not critical, since a relatively long plug-in unit can be selected.

The flexible design of the analysis device of the invention results from the fact that the basic units, such as the pump, the injection valve and the detector are each attached to a base plate and the base plate has a guide means. The base plates are in turn arranged on a support mounting in such a manner that, like optical components on optical benches, the basic units are displaceable by means of riders. After being joined together, the base plates are fixed to the support mounting, the securing means of course being releasable again.

Figure 3:
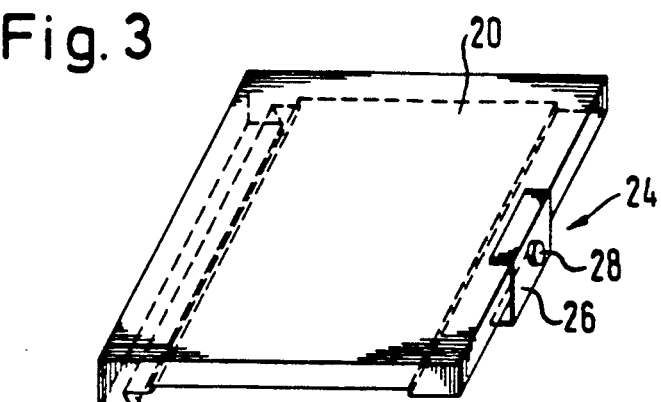
FIG. 3 is an illustration, using a base plate (a) and a base plate with a support plate (b), of the basic structure of an analysis device of the invention, partially disassembled.

The support mounting in each case is preferably made with a track and the base plates with a dovetail guide means 22 as shown in FIG. 3, of the accompanying drawings. Other guide means are, however, also conceivable. A simple means of fixing the base plates to the support mounting is a clamping means.

The connecting hoses of the individual basic units, such as the pump, the injection valve and the detector are advantageously joined together to form a hose track, i.e., a hose bus. If the connections are of uniform design such a collective hose line allows a space-saving and exceptionally flexible connection for the hose lines.

In the same way, the electrical connection lines are preferably designed as a bus. Such collective lines may comprise, for example, ribbon cables, multicore cables, etc. and plug connections. In one embodiment of the analysis device according to the invention the hose track is arranged on one side of the device and the electrical bus on the other.

As mentioned, the width and height dimensions in each case are advantageously the same as the width and the height of standard plug-in units or are simple fractions thereof, which means that the installation of the device is exceptionally economical. The handling of the device is substantially simplified by the fact that the support mounting is secured to a front plate, perpendicular to that front plate, and has a sliding guide. The device then needs merely to be pushed in or pulled out forwards or backwards, respectively.

The basic units can be arranged directly on a base plate. Depending on the dimensions it is also possible for a perpendicular support plate to be arranged on the base plate. Secured to such a support plate is, for example, the pump or the injection valve. Advantageously, the pump and/or the valve is/are secured to one side of the support plate and the respective drive motor is secured to the other side of the support plate. In each case a pin fits through the support plate into the pump and/or valve shaft coupling. This allows generally available pumps, valves and motors to be used. The mode of coupling is known.

Although the invention provides for the use of basic units that are currently standard, basic units specially adapted for the flexible structure of the analysis device according to the invention have been developed.

For example, a thermostat has been developed that is mounted on a base plate and comprises a heat-insulated outer housing with heating spirals 58 (see FIG. 4) and an internal member that is pushed into the outer housing, onto which internal member the hose is wound to form the reaction loop. The thermostat arrangement of course also contains the requisite electronics for the temperature preselection and its control. Provision is made, for example, for four freely selectable temperatures (for example 25°, 37°, 50° and 80° C.) to be set using a jumper and/or a programmer. As a precaution, a voltage source of 24 V AC is envisaged, as for all basic units. The newly developed thermostat differs essentially from the thermostats having a continually adjustable temperature selection available from Tecator GmbH, supra.

A diffusion and pH-sensor stage that is mounted on a base plate has also been developed. The stage comprises a housing within which a gas exchanger is arranged. The exchanger includes conduits for gas donor and gas acceptor streams. The conduits receive two through-flow electrodes which are attached to the housing, a pH sensitive electrode having a liquid membrane and a reference electrode. The pH-sensitive electrode advantageously has a plastics membrane the manufacture of which is described, for example, in 'A Hydrogen Ion-Selective Liquid-Membrane Electrode Based on Tri-n-dodecylamine as Neutral Carrier' by P. Schulthess et al., Analytica Chimica Acta 131, 1981, pages 11 to 116. In function, an electrode equipped with such a liquid membrane is of no more value than a conventional glass electrode in the pH range of interest for flow-injection analysis. A liquid-membrane electrode does, however, have considerable advantages over a glass electrode because it is easy to manufacture, economical, small and resistant to breaking. In addition, because of their dimensions (customary shaft lengths 130 to 150 mm) and spherical diaphragm, glass electrodes are not suitable for direct use in flow systems. The diffusion- and pH-sensor stage of the invention advantageously has an integrated gas exchanger which allows for special analysis techniques, for example the detection of ammonium ions in the form of $NH_3$, carbonate ions in the form of $CO_2$, and so on, or the detection of substrates or enzymes that yield the corresponding ions as products.

As a result of the invention a photometer has also been developed as a basic unit of the novel analysis device. The photometer is mounted on a base plate and comprises a housing in which a through-flow cell having a perpendicular cell bore is arranged. Arranged at one end of the cell bore is an illumination source and at the other end a photoelectric sensor. Luminescent diodes, which are available in the colors deep and light red (660 and 635 nm, respectively), yellow (590 nm) and green (560 nm) and/or blue (480 nm) are preferably used as the illumination source. The color purity of the light, measured by the width of the absorption bands of dyestuffs that absorb in the visible range, is sufficiently high for spectral filters to be dispensed with. Instead of or in addition to the luminescent diodes, the invention also provides for the optional use of photoconductive fiber cables to which external lamps can be connected. Using stop filters it is possible to convert the photometer into a fluorescence spectrometer.

A development of the analysis device according to the invention is possible with the incorporation of enzyme reactors, if desired as an extension of the existing thermostat, ion- and gas-sensitive electrodes in the existing electrode basic unit and other special detectors, such as conductivity detectors, electrochemical cells, luminescence detectors and so on. Coupled to the analysis device according to the invention, especially in the multi-channel embodiment, is, advantageously, a computer. This controls valves and pumps timewise, carries out certain analysis techniques and evaluates, for example, the measured signals. The results can then be printed, plotted, stored and/or transmitted by way of standard interfaces to further computers, data stations, control and monitoring equipment.

The invention is explained further below with reference to preferred embodiments and the drawings.

Figure 1:
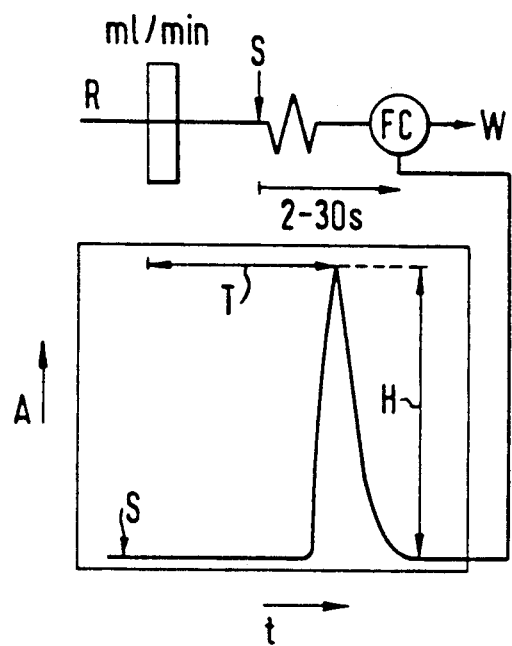
FIG. 1 is an illustration of the basic functioning of a prior art device for flow-injection analysis.
Figure 2:
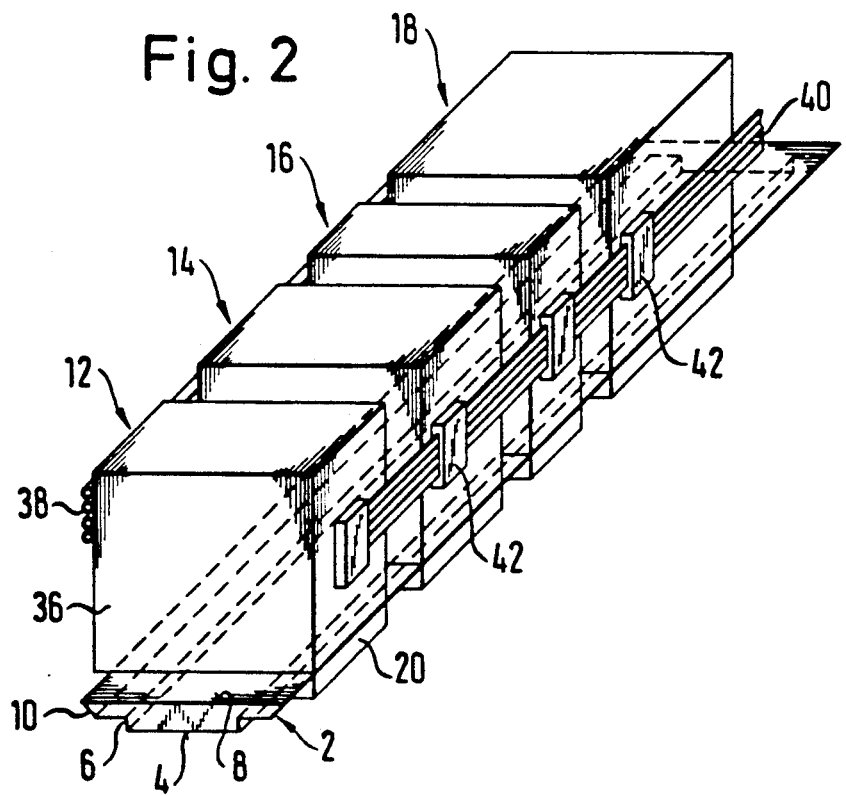
FIG. 2 is a perspective view of an assembled analysis device of the invention.

FIG. 2 shows a flow-injection analysis device according to the invention in the unmounted state. It comprises an elongate support mounting 2 in the form of a track. The support mounting 2 is made from plate material and is flat on the top 8 and bottom 4. At the edges the support mounting is provided with a profile which in the embodiment shown is the mating fit of a dovetail guide means 10. On the bottom the support mounting also has recesses 6 which serve as a sliding guide for the support mounting in a housing, for example a 19" housing. Round or other profiles can be secured in such a housing in the form of counterparts and/or guide elements to guide the support mounting 2.

Arranged on the support mounting 2 are basic units 12, 14, 16 and 18 which together form the actual device. The basic units 12 to 18 contain, for example, the pump, the injection valve and a detector, each of which is attached to a base plate 20. Such a base plate 20 is shown on an enlarged scale in FIG. 3. The base plate 20 is of slab-like design, for example of metal, and is provided on the underside with a guide means 22 which in the embodiment shown is a dovetail guide means. With this guide means the base plate 20 is mounted on the support mounting 2 in such a manner as to be displaceable. For holding the base plate 20 on the support mounting 2 a clamping device 24 is arranged at the side of the base plate 20. In the embodiment shown the clamping device 24 is in the form of a bracket 26 which fits round the base plate 20 and the track of the support mounting 2 and is clamped by means of a screw 28.

The components of the analysis device are mounted on the base plates either directly or on perpendicular support plates 30. Such a support plate 30 is shown in FIG. 3. In the embodiment shown, a pump body 32 is attached to the front of the support plate 30 and a pump motor 34 is attached to the back of the support plate.

The ends of the base plates 20 are flush with the ends of the pumps, valves or other components of the device arranged on them, together with any housings 36 surrounding the components of the device. The maximum width and height of the pumps, valves or other components of the device, together with any housings 36 and/or the support plates 30, are the same in each case, whereas the depths vary according to the components used. On the left in FIG. 2 is a string 38 of connecting hoses from the units of the device, which hoses are joined together to form a hose track. On the other side of the housing in each case is an electrical bus 40 extending in the longitudinal direction with respect to the support mounting 2. In the embodiment shown, the bus comprises ribbon cables which are joined together by means of plug connections 42. By way of the plug connections 42 the bus is also connected to the individual components of the analysis device.

Figure 4:
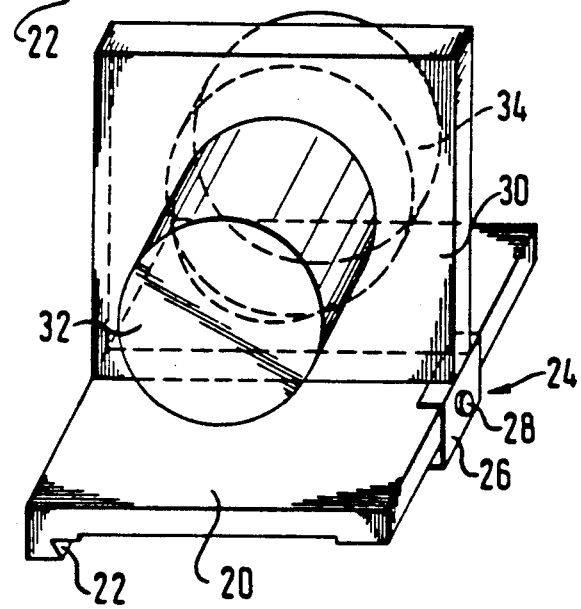
FIG. 4 shows a thermostat for the device of the invention.
Figure 7:
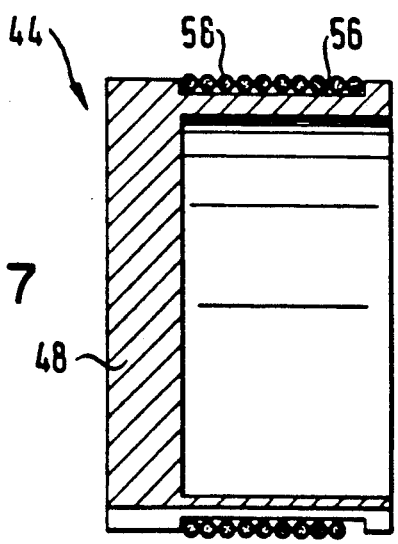
Figure 8:
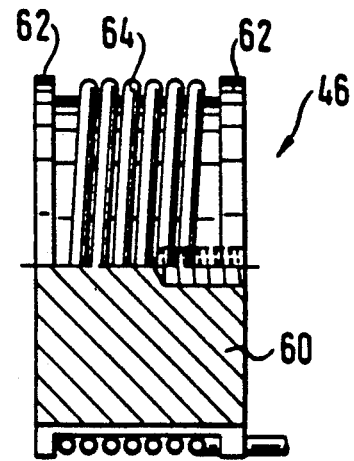

FIG. 4 shows a thermostat which was developed for use in an analysis device according to the invention. The thermostat comprises essentially two parts, namely a cylindrical outer housing 44 and a cylindrical internal member 46. The outer housing 44 is made of metal and is heat-insulated on all sides. It has a back wall 48 of relatively great thickness and a recess 56 in which heating spirals 58 are arranged adjacent to one another. The cylindrical internal member 46 is provided with a flange 62 at the front and a flange 62 at the back. Between the flanges 62 a portion 64 of hose is wound onto the internal member 46, serving as a reel, to form a reaction loop.

Figure 5:
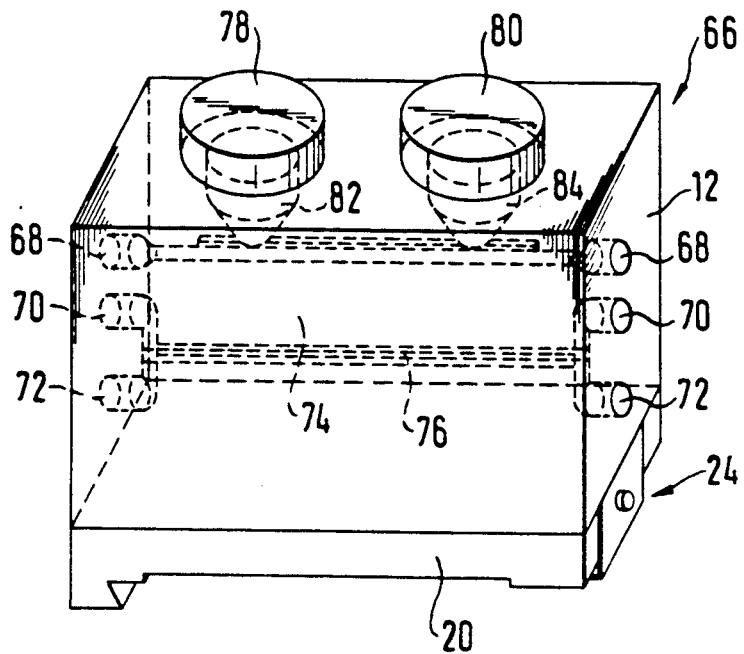
FIG. 5 shows a diffusion- and pH sensor stage for the analysis device of the invention.

FIG. 5 shows a diffusion- and pH-sensor stage 66. The housing 12 is provided with electrode connections 68 and channel connections 70, 72 for a gas exchanger 74. The gas exchanger 74 comprises exchanger channels for the gas-donor stream (70—70) and the gas-acceptor stream (72—72). Arranged between the connections 70 and 72 is a exchanger membrane 76, which is gas-permeable.

On the top of the housing 12 are connections 78 and 80 for a measuring electrode 82 and a reference electrode 84. The measuring electrode 82 designed as a pH electrode is equipped with a so-called liquid membrane which in the embodiment shown is a plastics membrane.

Figure 6:
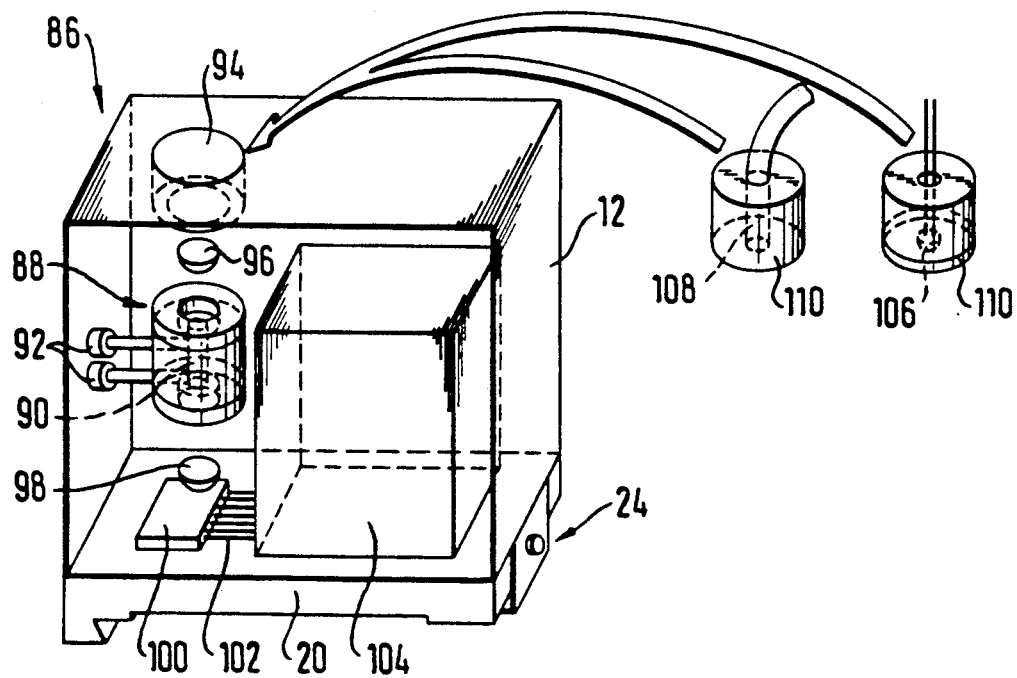
FIG. 6 shows a photometer for the analysis device of the invention.

The detector shown in FIG. 6 is a photometer 86. The photometer comprises a 10 mm through-flow cell 88 with a perpendicular cell bore 90, the ends of which are connected to connections 92 on the housing wall. An illumination source 94 emits light through a condensing lens 96 to the upper end of the cell bore 90. The light passes through the cell bore 90 and a further lens 98 arranged below it and falls onto a photoelectric sensor 100. The photoelectric sensor 100 is connected by way of a connecting cable 102 to an electronic unit 104.

The illumination source 94 can be in the form of luminescent diodes 106 which are available for emitting light in various wave lengths. Alternatively, a photoconductive fiber cable 108 can be used which is illuminated externally by a lamp (not shown) in the UV or the visual range. The illumination source 94 is designed to be exchangeable, the luminescent diodes 106 and the photoconductive fibre cable 108 being installed in housings 110 of the same dimensions.

What is claimed is:

1. Flow-injection analysis apparatus, which comprises; a reaction loop in flow communication with
   (i) a pump attached to a first base plate;
   (ii) an injection valve attached to a second base plate; and
   (iii) a detector attached to a third base plate;
      each of the first, second and third base plates being provided with a guide means, for slidable mounting on a support mounting; the pump, the injection valve and the detector, each with its base plate being substantially uniform in width and height;
      the first, second and third base plates being removably joined together on the support mounting by a releasable securing means.

2. Apparatus according to claim 1, wherein the support mounting is a track and each of the base plates guide means is a dovetail.

3. Apparatus according to claim 1, wherein the base plates are clamped to the support mounting.

4. Apparatus according to claim 1, which further comprises a plurality of hoses connecting the pump, the injection valve and the detector to the reaction loop, said plurality of hoses being joined together to form a hose track.

5. Apparatus according to claim 1, which further comprises electrical connecting lines from the pump, the injection valve and the detector in the form of a bus.

6. Apparatus according to claim 5, wherein the bus further comprises ribbon cables or multicore cables and plug connections.

7. Apparatus according to claim 5, wherein the hose track or the bus is arranged on one side of the pump, injection valve or detect in the longitudinal direction of the support mounting.

8. Apparatus according to claim 1, wherein the support mounting is secured to a front plate, perpendicular to the front plate, and includes a sliding guide.

9. Apparatus according to claim 1, which further comprises a perpendicular support plate secured to the base plates and wherein the pump or the injection valve is secured to the perpendicular support plate.

10. Apparatus according to claim 9, which further comprises a pump drive motor means for operating the pump and wherein the pump or the injection valve is secured to one side of the perpendicular support plate and the drive motor means is secured to the opposite side of the perpendicular support plate and wherein in each case a pin fits through the perpendicular support plate into the pump or a valve shaft coupling.

11. Apparatus according to claim 1, wherein the reaction loop comprises a hose wound on an internal member inserted into a heat-insulated outer housing which contains heating means and a thermostat mounted on the base plates.

12. Apparatus according to claim 1, which further comprises a diffusion- and pH-sensor stage mounted on the third base plate and wherein the diffusion- and pH-sensor stage comprises (a) housing; (b) a gas exchanger arranged in said housing; (c) a first conduit for a gas-donor stream passing into said housing; (d) a second conduit for a gas-acceptor stream passing into said housing; said first and second conduits each entering into said gas exchanger; (e) a pH-sensitive through-flow electrode having a liquid membrane; (f) and a through-flow reference electrode, said electrodes projecting into said housing.

13. Apparatus according to claim 12, wherein the pH-sensitive electrode has a plastic membrane.

14. Apparatus according to claim 1, wherein the detector is a photometer which comprises a housing in which is arranged a through-flow cell having a perpendicular cell bore and an illumination source which is arranged at one end of the cell bore and a photoelectric sensor which is arranged at the other end of the cell bore.

15. Apparatus according to claim 14, wherein the illumination source is a luminescent diode.

16. Apparatus according to claim 14 wherein the illumination source comprises photoconductive fiber cables connected to external lamps.

* * * * *